US012216819B2

(12) United States Patent
Unberath et al.

(10) Patent No.: US 12,216,819 B2
(45) Date of Patent: Feb. 4, 2025

(54) METHODS, SYSTEMS, AND RELATED ASPECTS FOR DETERMINING A COGNITIVE LOAD OF A SENSORIZED DEVICE USER

(71) Applicant: THE JOHNS HOPKINS UNIVERSITY, Baltimore, MD (US)

(72) Inventors: Mathias Unberath, Baltimore, MD (US); Kinjal Shah, Belle Mead, NJ (US); Wenhao Gu, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 18/556,973

(22) PCT Filed: Apr. 28, 2022

(86) PCT No.: PCT/US2022/026763

§ 371 (c)(1),
(2) Date: Oct. 24, 2023

(87) PCT Pub. No.: WO2022/232414

PCT Pub. Date: Nov. 3, 2022

(65) Prior Publication Data

US 2024/0211040 A1 Jun. 27, 2024

Related U.S. Application Data

(60) Provisional application No. 63/181,085, filed on Apr. 28, 2021.

(51) Int. Cl.
*G06F 3/01* (2006.01)
*A61B 5/16* (2006.01)
*G06V 40/18* (2022.01)

(52) U.S. Cl.
CPC .............. *G06F 3/013* (2013.01); *A61B 5/163* (2017.08); *G06V 40/18* (2022.01)

(58) Field of Classification Search
CPC .......... G06F 3/013; G06V 40/18; A61B 5/163
See application file for complete search history.

(56) References Cited

U.S. PATENT DOCUMENTS 10,976,816 B2 * 4/2021 Wilson .................... G06T 19/20
11,327,636 B2 * 5/2022 Pruitt ...................... G06F 1/324
2003/0167167 A1 * 9/2003 Gong ...................... G10L 15/22
704/250

(Continued)

OTHER PUBLICATIONS

Baharlou, S. (Authorized officer), International Preliminary Report on Patentability in corresponding International Application No. PCT/US2022/026763 mailed on Nov. 9, 2023, 8 pages.

(Continued)

*Primary Examiner* — Gene W Lee
(74) *Attorney, Agent, or Firm* — MH2 Technology Law Group LLP; Christopher C. Sappenfield

(57) ABSTRACT

Provided herein are methods of determining a cognitive load of a sensorized device user in certain aspects. Provided herein are also methods of adjusting an interface between a user and a sensorized device in some aspects. Related devices, systems, and computer program products are also provided.

16 Claims, 8 Drawing Sheets

(56) References Cited

U.S. PATENT DOCUMENTS

| | | | | |
|---|---|---|---|---|
| 2010/0217097 | A1* | 8/2010 | Chen | G16H 50/20<br>600/300 |
| 2013/0325482 | A1* | 12/2013 | Tzirkel-Hancock | G10L 21/18<br>704/275 |
| 2020/0174557 | A1 | 6/2020 | Alailima et al. | |
| 2020/0216082 | A1* | 7/2020 | Amir | G05B 13/0265 |
| 2020/0219608 | A1* | 7/2020 | Amir | A61B 5/168 |
| 2020/0409455 | A1* | 12/2020 | Wilson | G06T 19/20 |
| 2023/0273682 | A1* | 8/2023 | Wei | A61B 5/7267<br>345/8 |
| 2023/0274186 | A1* | 8/2023 | Wei | G06N 20/00<br>706/12 |

OTHER PUBLICATIONS

Rodriquez, K. (Authorized officer), International Search Report and Written Opinion in corresponding International Application No. PCT/US2022/026763 mailed on Aug. 30, 2022, 10 pages.

Sharath et al., "A recurrent neural network for attenuating non-cognitive components of pupil dynamics." Frontiers in Psychology 12 (2021): 604522.

* cited by examiner

METHODS, SYSTEMS, AND RELATED ASPECTS FOR DETERMINING A COGNITIVE LOAD OF A SENSORIZED DEVICE USER

CROSS-REFERENCE TO RELATED APPLICATIONS

This application is the national stage entry of International Patent Application No. PCT/US2022/026763, filed on Apr. 28, 2022, and published as WO 2022/232414 A9 on Nov. 3, 2022, which claims the benefit of U.S. Provisional Patent Application Ser. No. 63/181,085, filed Apr. 28, 2021, both of which is are hereby incorporated herein by reference herein in their entireties.

BACKGROUND

Human-computer interactions in ubiquitous mixed or full virtual reality environments, as they are delivered by see-through head-mounted displays or smart headphones, are often mediated by virtual personal agents. These agents, however, currently lack understanding of the user's cognitive load which results in frustration, task abandonment, and poor adoption. Cognitive load awareness could substantially increase the perceived emotional intelligence of these agents to enable more natural user interactions. Eye tracking is a promising avenue for cognitive load monitoring in mixed reality environments because eye cameras are readily or easily integrated in the devices. Further, pupillometry has been widely used to estimate cognitive effort in laboratory conditions. However, it is not currently possible to estimate cognitive load changes based on eye tracking data in unconstrained, real life-like environmental conditions because changes in pupillometric data may not only result from cognitive effort, but changes in other environmental conditions, such as ambient light or focal brightness.

Accordingly, there is a need for additional methods, and related aspects, for determining and monitoring cognitive load changes in subjects.

SUMMARY

The present disclosure relates, in certain aspects, to methods, devices, systems, and computer readable media of use in determining a cognitive load of a sensorized or detection device user and/or adjusting an interface between a user and a sensorized or detection device. The sensorized or detection device typically has the capability of substantially simultaneously sensing both pupillometric data values from a user and environmental data values (e.g., from an unconstrained or in-the-wild environment proximal to the user), such as emitted light that is collected by at least one pupil of the user, and deconfounding those data values to distinguish between pupillometric data values (e.g., pupil dilation or the like) attributable to the environment of the user and those attributable to the cognitive load of the user. Non-limiting examples of such sensorized or detection devices include virtual reality (VR) headsets and eyeglass frames comprising one or more video cameras, among many others. In some exemplary embodiments, sensorized devices comprise, or are capable of accessing, intelligent personal assistants (IPAs) (e.g., software agents or the like). In some embodiments, IPAs function through and/or are embodied by devices that are separate from sensorized devices. These and other aspects will be apparent upon a complete review of the present disclosure, including the accompanying figures.

In one aspect, the present disclosure provides method of determining a cognitive load of a sensorized device user at least partially using a computer. The method includes receiving, by the computer, at least a first substantially real-time pupillometric data value from the user from at least a first time point. The method also includes receiving, by the computer, at least a first substantially real-time unconstrained environmental data value from at least one location proximal to the user from the first time point (e.g., from a mixed reality or partially virtual environment, from a fully virtual environment, or the like). In addition, the method also includes isolating, by the computer, one or more cognitive load factors from one or more non-cognitive load factors influencing the user at the first time point based at least upon the first substantially real-time pupillometric data value and the first substantially real-time unconstrained environmental data value, thereby determining the cognitive load of the sensorized device user. In some exemplary embodiments, the sensorized device comprises an intelligent personal assistant (IPA). In other exemplary embodiments, the sensorized device comprises a virtual reality (VR) device (e.g., a VR headset or the like).

In another aspect, the present disclosure provides a method of adjusting an interface between a user and a sensorized device (e.g., an intelligent personal assistant (IPA) device, a virtual reality (VR) device (e.g., a VR headset or the like), or the like). The method includes receiving at least a first substantially real-time pupillometric data value from the user from at least a first time point and at least a first substantially real-time unconstrained environmental data value from at least one location proximal to the user from the first time point. The method also includes receiving at least a second substantially real-time pupillometric data value from the user from at least a second time point and at least a second substantially real-time unconstrained environmental data value from at least one location proximal to the user from the second time point, wherein the user is using the sensorized device at least proximal to the first time point and/or the second time point. The method also includes isolating one or more cognitive load factors from one or more non-cognitive load factors influencing the user at the first and second time points based at least upon the first substantially real-time pupillometric data value, the first substantially real-time unconstrained environmental data value, the second substantially real-time pupillometric data value, and/or the second substantially real-time unconstrained environmental data value to determine a cognitive load change in the user between the first and second time points to produce a determined cognitive load change. In addition, the method also includes adjusting at least one function of the sensorized device at least proximal to the first time point and/or the second time point based at least in part on the determined cognitive load change in the user, thereby adjusting the interface between the user and the sensorized device.

In some embodiments, the user is using at least one sensorized device at least proximal to the first time point and wherein the method further comprises adjusting at least one function of the sensorized device at least proximal to the first time point based at least in part on the determined cognitive load of the user. In some embodiments, the sensorized device comprises the computer. In some embodiments, the sensorized device and the computer are operably connected to one another.

In some embodiments, the methods disclosed herein further include receiving, by the computer, at least a second substantially real-time pupillometric data value from the user from at least a second time point, and receiving, by the computer, at least a second substantially real-time unconstrained environmental data value from at least one location proximal to the user from the second time point. In these embodiments, the methods also include isolating, by the computer, one or more of the cognitive load factors from one or more of the non-cognitive load factors influencing the user at the first and second time points based at least upon the first substantially real-time pupillometric data value, the first substantially real-time unconstrained environmental data value, the second substantially real-time pupillometric data value, and/or the second substantially real-time unconstrained environmental data value to determine a cognitive load change in the user between the first and second time points. In some embodiments, the methods disclosed herein include determining the cognitive load change in the user between the first and second time points by determining an inverse probability of the cognitive load change given the first substantially real-time pupillometric data value, the first substantially real-time unconstrained environmental data value, the second substantially real-time pupillometric data value, and/or the second substantially real-time unconstrained environmental data value. A variety of machine learning methods that predict or determine the presence of a cognitive load change in a user are also optionally utilized in performing the methods disclosed herein.

In some embodiments of the methods disclosed herein, the first and/or second substantially real-time pupillometric data value comprises a pupil diameter, a pupil radius, a pupil size, a blink rate, a saccade rate, or other measure of at least one eye of the user. In some embodiments of the methods disclosed herein, the first and/or second substantially real-time unconstrained environmental data value comprises a measure of at least one visual property. In some embodiments of the methods disclosed herein, the visual property comprises an ambient light measure and/or a focal brightness measure.

In some embodiments of the methods disclosed herein, the first and/or second substantially real-time unconstrained environmental data value comprises a measure of at least one visual property, at least one auditory property, at least one dictation property, at least one physiological property or state of the user, and/or at least one physical property of an environment external to the user. In some embodiments, the methods disclosed herein include receiving the first and/or second substantially real-time pupillometric data value and/or the first and/or second substantially real-time unconstrained environmental data value from at least one detection device.

In some embodiments of the methods disclosed herein, the detection device comprises at least one video camera. In some embodiments of the methods disclosed herein, a wearable device comprises the detection device, which wearable device is worn by the user. In some embodiments of the methods disclosed herein, the wearable device comprises a head-mounted display, a headphone, a spectacle frame, and/or an article of clothing.

In another aspect, the present disclosure provides a system, comprising at least one controller that comprises, or is capable of accessing, computer readable media comprising non-transitory computer executable instructions which, when executed by at least one electronic processor, perform at least: receiving at least a first substantially real-time pupillometric data value from a user of a sensorized device from at least a first time point; receiving at least a first substantially real-time unconstrained environmental data value from at least one location proximal to the user from the first time point; and isolating one or more cognitive load factors from one or more non-cognitive load factors influencing the user at the first time point based at least upon the first substantially real-time pupillometric data value and the first substantially real-time unconstrained environmental data value.

In another aspect, the present disclosure provides a system, comprising at least one controller that comprises, or is capable of accessing, computer readable media comprising non-transitory computer executable instructions which, when executed by at least one electronic processor, perform at least: receiving at least a first substantially real-time pupillometric data value from a user of a sensorized device from at least a first time point and at least a first substantially real-time unconstrained environmental data value from at least one location proximal to the user from the first time point, and at least a second substantially real-time pupillometric data value from the user from at least a second time point and at least a second substantially real-time unconstrained environmental data value from at least one location proximal to the user from the second time point, when the user is using the sensorized device at least proximal to the first time point and/or the second time point; isolating one or more cognitive load factors from one or more non-cognitive load factors influencing the user at the first and second time points based at least upon the first substantially real-time pupillometric data value, the first substantially real-time unconstrained environmental data value, the second substantially real-time pupillometric data value, and/or the second substantially real-time unconstrained environmental data value to determine a cognitive load change in the user between the first and second time points to produce a determined cognitive load change; and adjusting at least one function of the sensorized device at least proximal to the first time point and/or the second time point based at least in part on the determined cognitive load change in the user.

In another aspect, the present disclosure provides a computer readable media comprising non-transitory computer executable instruction which, when executed by at least one electronic processor perform at least: receiving at least a first substantially real-time pupillometric data value from a user of a sensorized device from at least a first time point; receiving at least a first substantially real-time unconstrained environmental data value from at least one location proximal to the user from the first time point; and isolating one or more cognitive load factors from one or more non-cognitive load factors influencing the user at the first time point based at least upon the first substantially real-time pupillometric data value and the first substantially real-time unconstrained environmental data value.

In another aspect, the present disclosure provides a computer readable media comprising non-transitory computer executable instruction which, when executed by at least one electronic processor perform at least: receiving at least a first substantially real-time pupillometric data value from a user of a sensorized device from at least a first time point and at least a first substantially real-time unconstrained environmental data value from at least one location proximal to the user from the first time point, and at least a second substantially real-time pupillometric data value from the user from at least a second time point and at least a second substantially real-time unconstrained environmental data value from at least one location proximal to the user from the second time point, when the user is using the sensorized device at least proximal to the first time point and/or the second time point; isolating one or more cognitive load factors from one or more non-cognitive load factors influencing the user at the first and second time points based at least upon the first substantially real-time pupillometric data value, the first substantially real-time unconstrained environmental data value, the second substantially real-time pupillometric data value, and/or the second substantially real-time unconstrained environmental data value to determine a cognitive load change in the user between the first and second time points to produce a determined cognitive load change; and adjusting at least one function of the sensorized device at least proximal to the first time point and/or the second time point based at least in part on the determined cognitive load change in the user.

In some embodiments of the system or computer readable media disclosed herein, the instructions further perform at least: adjusting at least one function of the sensorized device at least proximal to the first time point based at least in part on the determined cognitive load of the user. In some embodiments of the system or computer readable media disclosed herein, the instructions further perform at least: receiving at least a second substantially real-time pupillometric data value from the user from at least a second time point; receiving at least a second substantially real-time unconstrained environmental data value from at least one location proximal to the user from the second time point; and isolating one or more of the cognitive load factors from one or more of the non-cognitive load factors influencing the user at the first and second time points based at least upon the first substantially real-time pupillometric data value, the first substantially real-time unconstrained environmental data value, the second substantially real-time pupillometric data value, and/or the second substantially real-time unconstrained environmental data value to determine a cognitive load change in the user between the first and second time points. In some embodiments of the system or computer readable media disclosed herein, the instructions further perform at least: determining the cognitive load change in the user between the first and second time points by determining an inverse probability of the cognitive load change given the first substantially real-time pupillometric data value, the first substantially real-time unconstrained environmental data value, the second substantially real-time pupillometric data value, and/or the second substantially real-time unconstrained environmental data value.

In some embodiments of the system or computer readable media disclosed herein, the first and/or second substantially real-time pupillometric data value comprises a pupil diameter, a pupil radius, a pupil size, a blink rate, a saccade rate, or other measure of at least one eye of the user. In some embodiments of the system or computer readable media disclosed herein, the first and/or second substantially real-time unconstrained environmental data value comprises a measure of at least one visual property. In some embodiments of the system or computer readable media disclosed herein, the visual property comprises an ambient light measure and/or a focal brightness measure.

In some embodiments of the system or computer readable media disclosed herein, the first and/or second substantially real-time unconstrained environmental data value comprises a measure of at least one visual property, at least one auditory property, at least one dictation property, at least one physiological property or state of the user, and/or at least one physical property of an environment external to the user. In some embodiments of the system or computer readable media disclosed herein, the instructions further perform at least: receiving the first and/or second substantially real-time pupillometric data value and/or the first and/or second substantially real-time unconstrained environmental data value from at least one detection device. In some embodiments of the system or computer readable media disclosed herein, the detection device comprises at least one video camera. In some embodiments of the system or computer readable media disclosed herein, the sensorized device comprises an intelligent personal assistant (IPA) device. In some embodiments of the system or computer readable media disclosed herein, the sensorized device comprises a virtual reality (VR) device.

Some embodiments include a detection device operably connected, or connectable to, a system or computer readable media disclosed herein. In some of these embodiments, a wearable device comprises the detection device, which wearable device is worn by the user. In some of these embodiments, the wearable device comprises a head-mounted display, a headphone, a spectacle frame, and/or an article of clothing.

BRIEF DESCRIPTION OF THE DRAWINGS

The accompanying drawings, which are incorporated in and constitute a part of this specification, illustrate certain embodiments, and together with the written description, serve to explain certain principles of the methods, devices, systems, and related computer readable media disclosed herein. The description provided herein is better understood when read in conjunction with the accompanying drawings which are included by way of example and not by way of limitation. It will be understood that like reference numerals identify like components throughout the drawings, unless the context indicates otherwise. It will also be understood that some or all of the figures may be schematic representations for purposes of illustration and do not necessarily depict the actual relative sizes or locations of the elements shown.

DEFINITIONS

Figure 1A:
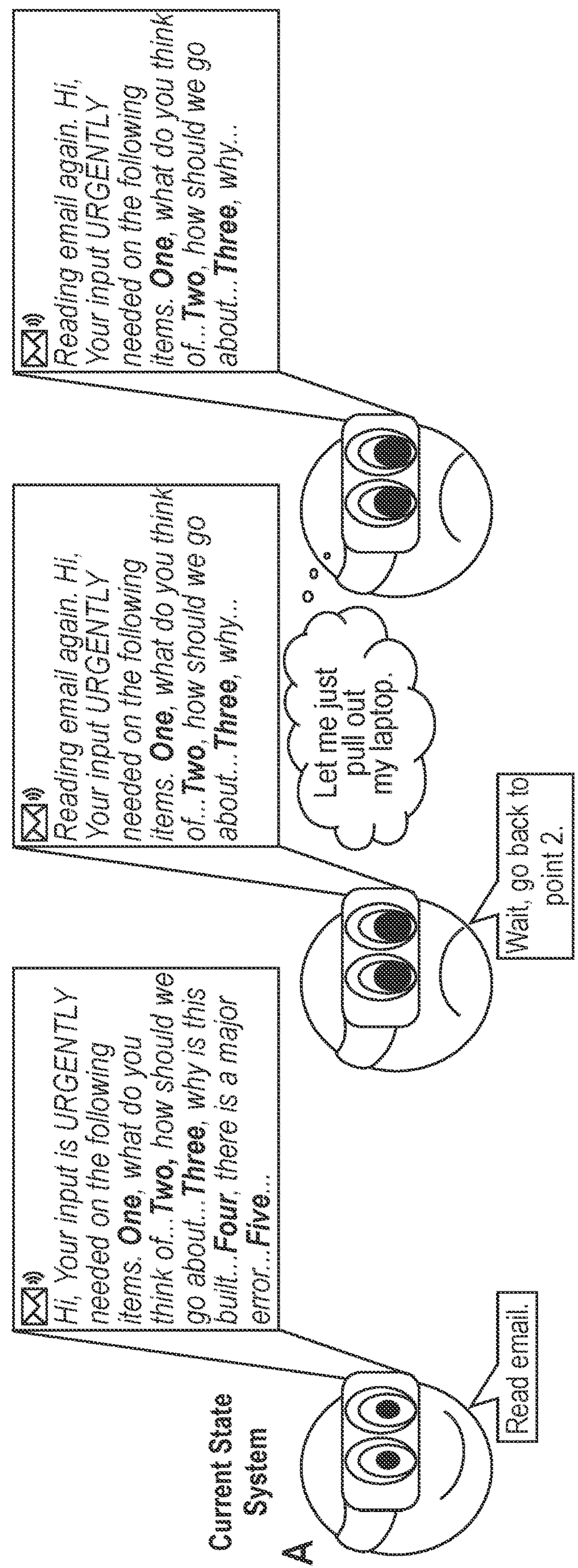
FIG. 1 (Panels A and B) schematically show the use of a pre-existing intelligent personal assistant system (Panel A) and a cognitive load aware system (Panel B) during an auditory task according to some aspects disclosed herein.

In order for the present disclosure to be more readily understood, certain terms are first defined below. Additional definitions for the following terms and other terms may be set forth through the specification. If a definition of a term set forth below is inconsistent with a definition in an application or patent that is incorporated by reference, the definition set forth in this application should be used to understand the meaning of the term.

As used in this specification and the appended claims, the singular forms "a," "an," and "the" include plural references unless the context clearly dictates otherwise. Thus, for example, a reference to "a method" includes one or more methods, and/or steps of the type described herein and/or which will become apparent to those persons skilled in the art upon reading this disclosure and so forth.

It is also to be understood that the terminology used herein is for the purpose of describing particular embodiments only and is not intended to be limiting. Further, unless defined otherwise, all technical and scientific terms used herein have the same meaning as commonly understood by one of ordinary skill in the art to which this disclosure pertains. In describing and claiming the methods, computer readable media, systems, and component parts, the following terminology, and grammatical variants thereof, will be used in accordance with the definitions set forth below.

About: As used herein, "about" or "approximately" or "substantially" as applied to one or more values or elements of interest, refers to a value or element that is similar to a stated reference value or element. In certain embodiments, the term "about" or "approximately" or "substantially" refers to a range of values or elements that falls within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value or element unless otherwise stated or otherwise evident from the context (except where such number would exceed 100% of a possible value or element).

Cognitive Load: As used herein, "cognitive load" refers to the used amount of working memory in a given subject, such as a human subject, at a particular point in time.

Cognitive Load Change: As used herein, "cognitive load change" refers to a change or difference in cognitive load experienced by a given subject between or among different time points.

Cognitive Load Factors: As used herein, "cognitive load factors" refer to factors or elements that contribute to the cognitive load experienced by a given subject. Cognitive load is typically thought to include extraneous, intrinsic, and germane factors. Cognitive load factors can contribute to, or otherwise influence, pupillometric data values obtained from or observed in a given subject.

Intelligent Personal Assistant Device: As used herein, an "intelligent personal assistant device" or "IPA device" refers to a software agent that performs tasks or services for a user in response to commands or questions posed or input (verbally or otherwise) to the agent by the user. An intelligent virtual assistant device is also sometimes referred to as an intelligent virtual assistant (IVA).

Machine Learning Algorithm: As used herein, "machine learning algorithm" generally refers to an algorithm, executed by computer, that automates analytical model building, e.g., for clustering, classification or pattern recognition. Machine learning algorithms may be supervised or unsupervised. Learning algorithms include, for example, artificial neural networks (e.g., back propagation networks), discriminant analyses (e.g., Bayesian classifier or Fisher's analysis), support vector machines, decision trees (e.g., recursive partitioning processes such as CART-classification and regression trees, or random forests), linear classifiers (e.g., multiple linear regression (MLR), partial least squares (PLS) regression, and principal components regression), hierarchical clustering, and cluster analysis. A dataset on which a machine learning algorithm learns can be referred to as "training data." A model produced using a machine learning algorithm is generally referred to herein as a "machine learning model."

Non-Cognitive Load Factors: As used herein, "non-cognitive load factors" refer to factors or elements that do not contribute to the cognitive load experienced by a given subject. Non-cognitive load factors can contribute to, or otherwise influence, pupillometric data values obtained from or observed in a given subject.

Pupillometric Data Value: As used herein, "pupillometric data value" refers to a value or measure of a property of a pupil of a given subject at a particular point in time. Such properties of the pupil include a dimension of the pupil (e.g., a diameter of the pupil, a radius of the pupil, an area or size of the pupil, or the like), a reactivity or dilation rate of the pupil, and the like.

Unconstrained Environmental Data Value: As used herein, "unconstrained environmental data value" refers to a value or measure of a property of a substantially uncontrolled environment experienced by a given subject at a particular point in time. Sometimes a subject that is in, or otherwise experiencing, an unconstrained environment is described as being "in the wild." Examples of unconstrained environmental data values, include a measure of a visual property, a measure of an auditory property, a measure of a dictation property, a measure of a physiological property or state of the user (e.g., body temperature, heart rate, blood pressure, or the like), a measure of a physical property of an environment external to the user (e.g., ambient light, focal brightness, etc.), and/or the like. Unconstrained environmental data values can contribute to, or otherwise influence, pupillometric data values obtained from or observed in a given subject.

Value: As used herein, "value" generally refers to an entry in a dataset that can be anything that characterizes the feature to which the value refers. This includes, without limitation, numbers, words or phrases, symbols (e.g., + or −) or degrees.

Virtual Reality Device: As used herein, "virtual reality device" or "VR device" refers to a device used to create a simulated experience or environment (e.g., immersive VR, text-based networked VR, or the like) for a user of the device that is similar or comparable to, or different from, a real world experience or environment. In some embodiments, a VR device comprises a VR headset or head-mounted display.

DETAILED DESCRIPTION

In some aspects, the present disclosure relates to the development of artificial intelligence methodologies that enable eye tracking-based cognitive load estimation in unconstrained, real life-like environments ("in the wild") to improve the function of sensorized devices (e.g., intelligent personal assistant devices (IPAs), VR devices, etc.) through more natural interaction mechanisms. Cognitive load estimation in unconstrained environments based on head-worn human- and world-facing sensors enables more natural interaction paradigms between humans and sensorized devices in mixed, augmented, or full virtual reality environments. In some embodiments, the technology disclosed herein involves a machine learning-based, algorithmic solution to estimate cognitive load changes in the wild based on a head-worn spectacle frame with integrated optical cameras that supply eye and world (human and world-facing, respectively) video feeds in real time. In some embodiments, the algorithms disclosed herein are based on a causal model of pupil dilation to estimate the inverse probability of cognitive load change given observed pupillometry and environmental conditions. Through these algorithms environmental conditions are estimated from the world and eye video feeds. These and other aspects will be apparent upon a complete review of the present disclosure, including the accompanying example and figures.

The present disclosure enables, in certain aspects, cognitive load estimation from eye-tracking data under normal environmental conditions. Human-computer interactions in ubiquitous mixed (e.g., extended or XR) reality environments, delivered by see-through head-mounted displays or smart headphones, are often mediated by virtual personal agents. These agents, however, currently lack understanding of the user's cognitive load which results in frustration, task abandonment, and poor adoption. Cognitive load awareness substantially increases the perceived emotional intelligence of these agents to enable more natural user interactions. Eye-tracking is a promising avenue for cognitive load monitoring in mixed reality environments because, for example, eye cameras are readily or easily integrated in the devices. Further, pupillometry has been widely used to estimate cognitive effort in laboratory conditions. However, prior to the present disclosure it was not possible to estimate cognitive load changes based on eye tracking data in unconstrained, real life-like environmental conditions using wearable eye-trackers because changes in pupillometric data values not only result from cognitive effort, but changes in other environmental conditions, such as ambient light or focal brightness.

Prior to the aspects disclosed herein, there were no products available that solve cognitive load estimation "in the wild" while interfacing with, for example, mixed reality device worn headsets. It was previously not possible to estimate cognitive load changes based on eye tracking data in unconstrained, real life-like environmental conditions (often referred to as "in the wild"). This is because changes in pupillometric data may not only result from cognitive effort, but changes in other environmental conditions, such as ambient light or focal brightness. Consequently, the environmental conditions that confound pupillometric data should be measured and processed synchronously. To illustrate, the pupillary response triggered by, for example, ambient light, are an order of magnitude (2-4 mm) larger than the response triggered by cognitive load changes (0.1-0.5 mm). However, pupillary responses to different factors are not additive, therefore, simply subtracting the expected effect of a given factor will not yield the desired isolation of pupil diameter changes due to cognitive load. Accordingly, in some embodiments, the present disclosure provides methods and related aspects that aggregate human- and world-facing sensory data to accurately estimate cognitive effort in the wild.

In contrast, other available products typically control environmental conditions by using remote, instead of wearable eye-trackers, controlling ambient light, limiting head motion, etc. In some embodiments, this disclosure combines eye-tracking data received from a wearable or mobile eye-tracker with a causal model of pupil dilation to estimate the inverse probability of cognitive load change given observed pupillometry and environmental conditions.

By way of additional background, user interfaces are typically designed with the objective of facilitating interactions while improving the experience of the user; however, previous interfaces cannot adapt to changing user needs, for example, when the cognitive load of the user suddenly increases substantially. This limitation becomes particularly apparent in ubiquitous mixed reality environments, such as those delivered via see-through head-mounted displays or smart headphones. Because these mixed reality environments blend seamlessly with routine tasks and environments of everyday life, the human-computer interaction (HCl) mechanisms should be particularly effective, unobtrusive, conforming to social norms, and should not require deliberate effort. Understanding the user's needs and cognitive effort is an important component to overcoming these barriers and paving the way for widespread adoption of transformative mixed reality technology. As a result, designing adaptive, workload aware user interfaces has become of increasing interest.

Cognitive load aware interaction paradigms are of particular importance for sensorized devices, like intelligent agents or intelligent personal assistants (IPAs). IPAs have gained increasing popularity over the past decade. Such systems provide an example of revolutionary technology that has caused users to face unintended challenges due to interface design. In some studies, the effect of common IPAs on a user's cognitive load during driving tasks were evaluated. These studies found a user's cognitive load to increase during interaction with the IPA, and found increased task abandonment when compared to the conventional, manual approach to completing the task. Commonly cited frustrations include the misinterpretation of commands and incorrect handling of pauses. These challenges have prevented personal agents or IPAs from seamlessly integrating into users' day-to-day lives. Moreover, the perceived intelligence of IPAs plays an important role in user adoption. The emotional intelligence of these agents, demonstrated, for example, by providing personalized timing strategies frequently play an equally important role in enabling natural user interactions. Thus, ubiquitous and unobtrusive cognitive load awareness amplifies the usefulness and adoption of IPAs by promoting natural experiences and seamless interactions that avoid user frustration.

Figure 1B:
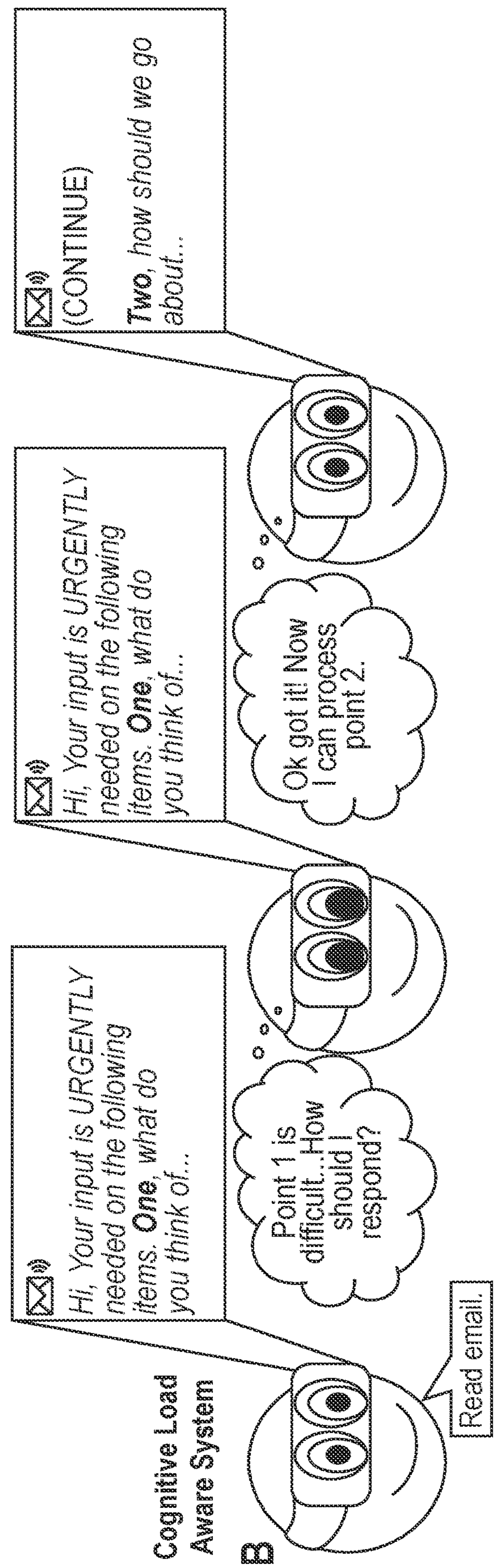

To further illustrate some of the problems associated with human-computer interactions, FIG. 1 (Panels A and B) schematically show the use of a pre-existing intelligent personal assistant system (Panel A) contrasted with a cognitive load aware system of the present disclosure (Panel B) during an auditory task according to some aspects disclosed herein.

A number of methods have previously been proposed to estimate cognitive load in constrained settings. These methods do not measure cognitive load directly, but infer cognitive load transitions from observations of other quantities, changes in which can be linked to cognitive load, if other environmental conditions can be precisely controlled for. Quantities that are routinely measured as a proxy for cognitive load include EEG activity, heart rate, galvanic skin response, body temperature, and eye movement. Eye tracking is particularly attractive, mainly because of at least three reasons: (1) eye tracking has been firmly established as an accurate indicator of cognitive effort, (2) being camera-based, eye tracking provides an unobtrusive mechanism for monitoring user responses to stimuli, and (3) eye trackers are rapidly becoming ubiquitous in consumer-grade mixed reality devices since gaze tracking enables more immersive experiences, such as foveated rendering or gaze-based object selection techniques.

Figure 2:
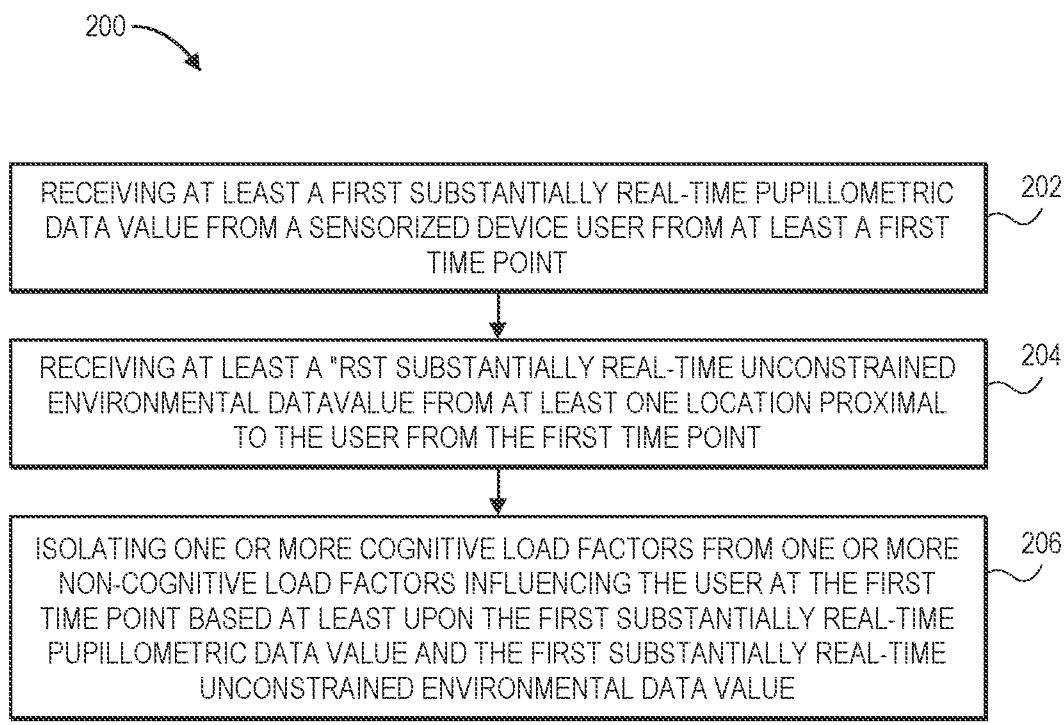
FIG. 2 is a flow chart that schematically depicts exemplary method steps of determining a cognitive load of a sensorized device user according to some aspects disclosed herein.

To illustrate, FIG. 2 is a flow chart that schematically depicts exemplary computer-implemented method steps of determining a cognitive load of a sensorized device user according to some aspects disclosed herein. As shown, method 200 includes receiving at least a first substantially real-time pupillometric data value from the user from at least a first time point (step 202). Method 200 also includes receiving at least a first substantially real-time unconstrained environmental data value from at least one location proximal to the user from the first time point (step 204). In addition, method 200 also includes isolating one or more cognitive load factors from one or more non-cognitive load factors influencing the user at the first time point based at least upon the first substantially real-time pupillometric data value and the first substantially real-time unconstrained environmental data value (step 206). Sensorized devices (e.g., IPAs, VR headsets, etc.) are commercially available from many different mixed reality device companies (e.g., Oculus, Apple, Acer, Microsoft, Magic Leap, Bose, Google, and HTC, among others) and from various smartphone manufacturers.

Figure 3:
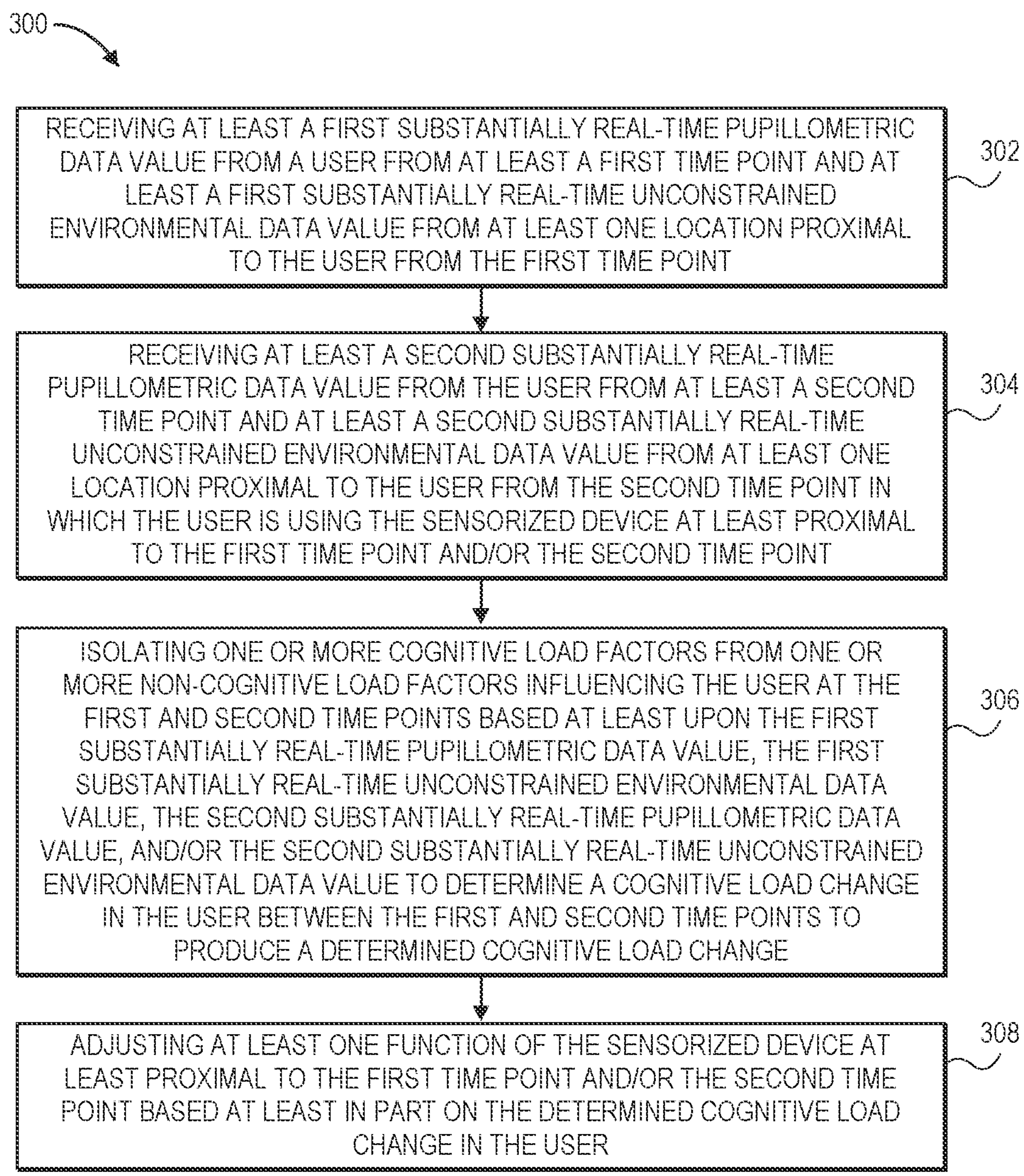
FIG. 3 is a flow chart that schematically depicts exemplary method steps of adjusting an interface between a user and a sensorized device according to some aspects disclosed herein.

To further illustrate, FIG. 3 is a flow chart that schematically depicts exemplary computer-implemented method steps of adjusting an interface between a user and a sensorized device according to some aspects disclosed herein. As shown, method 300 includes receiving at least a first substantially real-time pupillometric data value from the user from at least a first time point and at least a first substantially real-time unconstrained environmental data value from at least one location proximal to the user from the first time point (step 302). Method 300 also includes receiving at least a second substantially real-time pupillometric data value from the user from at least a second time point and at least a second substantially real-time unconstrained environmental data value from at least one location proximal to the user from the second time point in which the user is using the sensorized device at least proximal to the first time point and/or the second time point (step 304). Method 300 also includes isolating one or more cognitive load factors from one or more non-cognitive load factors influencing the user at the first and second time points based at least upon the first substantially real-time pupillometric data value, the first substantially real-time unconstrained environmental data value, the second substantially real-time pupillometric data value, and/or the second substantially real-time unconstrained environmental data value to determine a cognitive load change in the user between the first and second time points to produce a determined cognitive load change (step 306). In addition, method 300 also includes adjusting at least one function of the sensorized device at least proximal to the first time point and/or the second time point based at least in part on the determined cognitive load change in the user (step 308).

Figure 4:
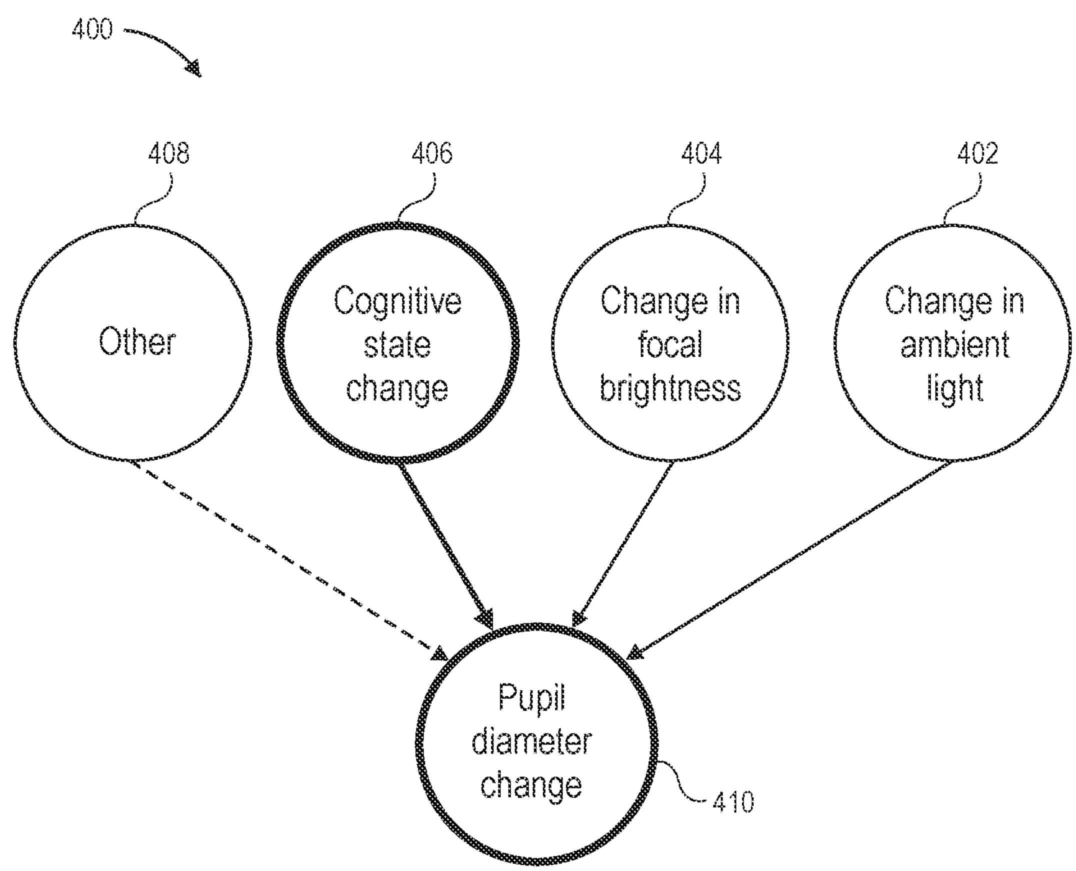
FIG. 4 is a diagram that schematically depicts an exemplary graphical causal model representing causes of pupil diameter change according to some aspects disclosed herein.

FIG. 4 is a diagram that schematically depicts an exemplary graphical causal model representing causes of pupil diameter change according to some aspects disclosed herein. As shown, model 400 includes changes in ambient light 402, changes in focal brightness 404, cognitive state changes in the user 406, and other causes 408 that can cause pupil diameter changes 410.

Typically, the user uses a sensorized device proximal to the first time point and/or the second time point, and the methods disclosed herein further include adjusting a function of the sensorized device (e.g., pausing the device's feedback, repeating a spoken text passage, etc.) at least proximal to the first time point and/or the second time point based at least in part on the determined cognitive load of the user. In some embodiments, the sensorized device comprises the computer, whereas in other embodiments, the sensorized device and the computer are operably connected to one another. Exemplary systems that include computers and sensorized devices are described further herein.

In some embodiments, the methods disclosed herein optionally further include receiving a second substantially real-time pupillometric data value from the user from at least a second time point, and receiving at least a second substantially real-time unconstrained environmental data value from at least one location proximal to the user from the second time point. In these embodiments, the methods also typically include isolating one or more of the cognitive load factors from one or more of the non-cognitive load factors influencing the user at the first and second time points based at least upon the first substantially real-time pupillometric data value, the first substantially real-time unconstrained environmental data value, the second substantially real-time pupillometric data value, and/or the second substantially real-time unconstrained environmental data value to determine a cognitive load change in the user between the first and second time points. In some embodiments, the methods disclosed herein include determining a cognitive load change in the user between the first and second time points by determining an inverse probability of the cognitive load change given the first substantially real-time pupillometric data value, the first substantially real-time unconstrained environmental data value, the second substantially real-time pupillometric data value, and/or the second substantially real-time unconstrained environmental data value.

In some embodiments of the methods disclosed herein, the first and/or second substantially real-time pupillometric data value comprises a pupil diameter, a pupil radius, a pupil size, a blink rate, a saccade rate, or other measure of at least one eye of the user. In some embodiments of the methods disclosed herein, the first and/or second substantially real-time unconstrained environmental data value comprises a measure of at least one visual property. In some embodiments of the methods disclosed herein, the visual property comprises an ambient light measure and/or a focal brightness measure.

In some embodiments of the methods disclosed herein, the first and/or second substantially real-time unconstrained environmental data value comprises a measure of at least one visual property, at least one auditory property, at least one dictation property, at least one physiological property or state of the user, and/or at least one physical property of an environment external to the user. In some embodiments, the methods disclosed herein include receiving the first and/or second substantially real-time pupillometric data value and/or the first and/or second substantially real-time unconstrained environmental data value from at least one detection device.

In some embodiments of the methods disclosed herein, the detection device comprises at least one video camera. In some embodiments of the methods disclosed herein, a wearable device comprises the detection device, which wearable device is worn by the user. In some embodiments of the methods disclosed herein, the wearable device comprises a head-mounted display, a headphone, a spectacle frame, and/or an article of clothing.

Figure 5A:
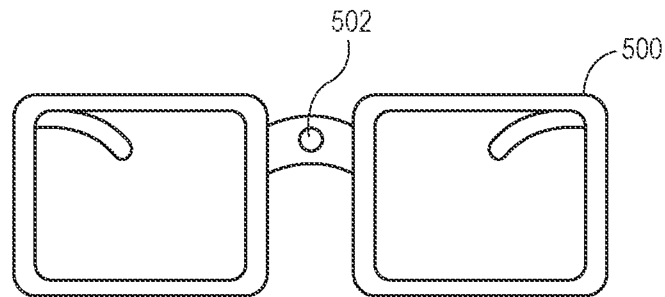
FIG. 5A-C schematically depict a wearable detection device from a side view (A), a back view (B), and diposed on a user from a side view, respectively, according to some aspects disclosed herein.
Figure 5B:
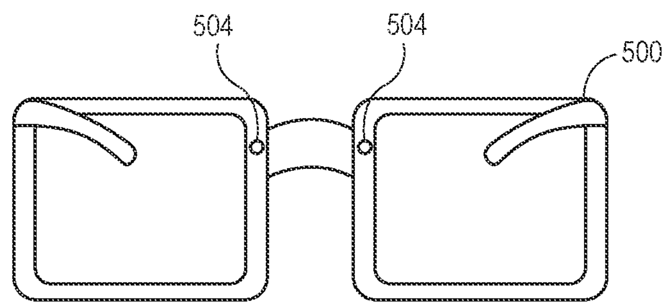
Figure 5C:
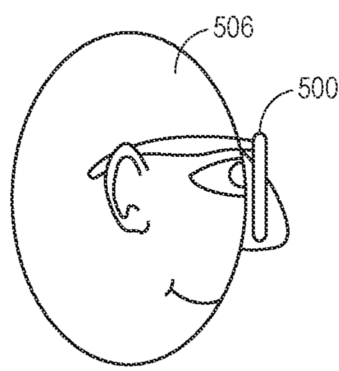

To illustrate, FIG. 5A-C schematically depict wearable detection device 500 from a side view (A), a back view (B), and diposed on user 506 from a side view, respectively, according to some aspects disclosed herein. As shown, detection device 500 includes world-facing video feed camera 502 that captures unconstrained environmental data values in substantially real-time. In addition, detection device 500 also includes user-facing video feed cameras 504 that captures pupillometric data values from user 506 in substantially real-time.

Figure 6:
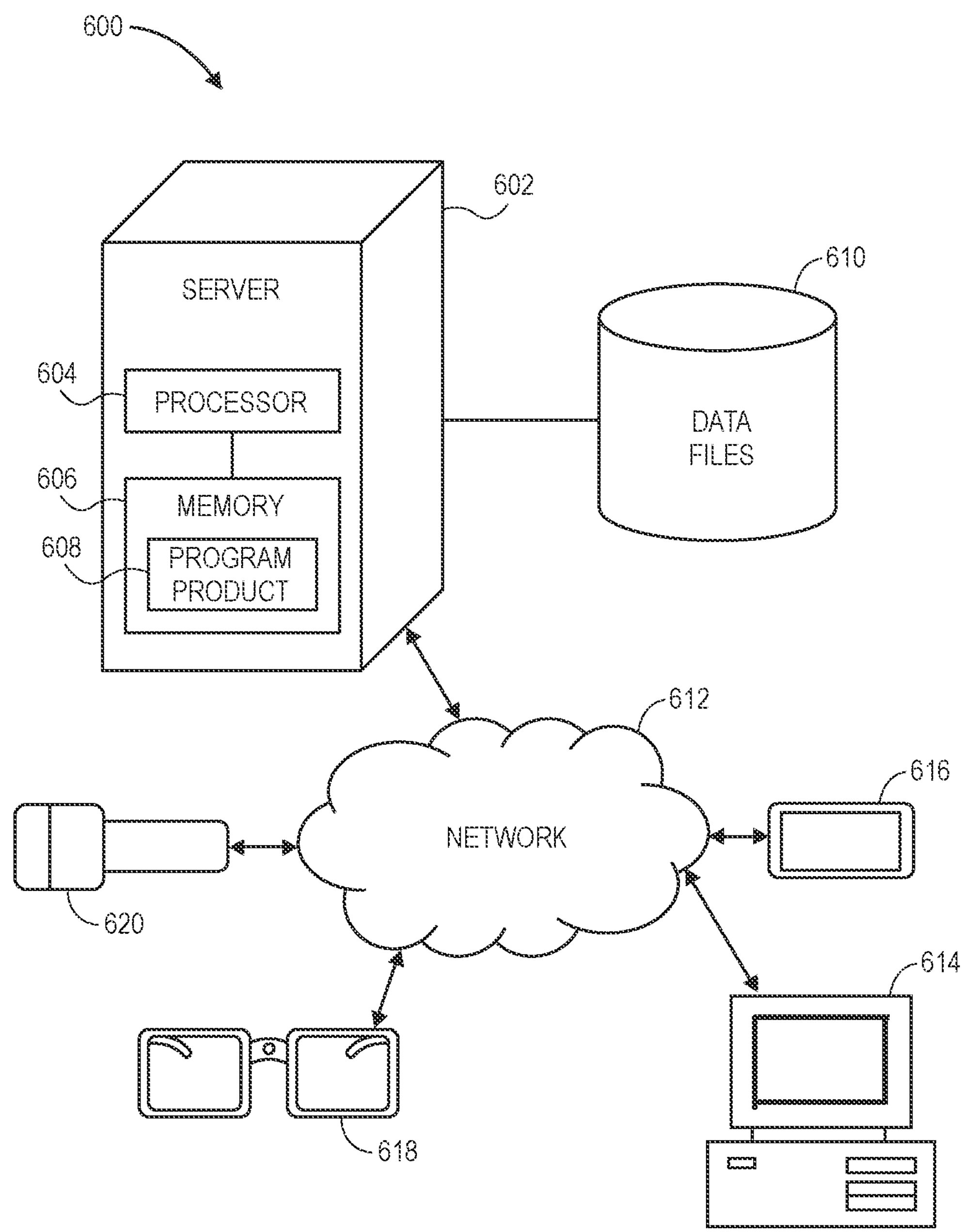
FIG. 6 is a schematic diagram of an exemplary system suitable for use with certain aspects disclosed herein.

The present disclosure also provides various systems and computer program products or machine readable media. In some aspects, for example, the methods described herein are optionally performed or facilitated at least in part using systems, distributed computing hardware and applications (e.g., cloud computing services), electronic communication networks, communication interfaces, computer program products, machine readable media, electronic storage media, software (e.g., machine-executable code or logic instructions) and/or the like. To illustrate, FIG. 6 provides a schematic diagram of an exemplary system suitable for use with implementing at least aspects of the methods disclosed in this application. As shown, system 600 includes at least one controller or computer, e.g., server 602 (e.g., a search engine server), which includes processor 604 and memory, storage device, or memory component 606, and one or more other communication devices 614, 616, (e.g., client-side intelligent personal assistant (IPA) devices, VR device, computer terminals, telephones, tablets, laptops, other mobile devices, etc. (e.g., for assisting a user in a virtual or mixed reality environment, etc.)) positioned proximal to (e.g., within sensory communication with a user), integrated with, or remote from wearable detection device 618 (shown as an eyeglass frame) or 620 (shown as a VR headset), and in communication with the remote server 602, through electronic communication network 612, such as the Internet or other internetwork. Communication or IPA devices 614, 616 typically include an electronic display (e.g., an internet enabled computer or the like), microphone, and/or speaker in communication with, e.g., server 602 computer over network 612 in which the electronic display comprises a user interface (e.g., a graphical user interface (GUI), a web-based user interface, and/or the like) for displaying results, functions, actions, etc. upon implementing the methods described herein. In certain aspects, communication networks also encompass the physical transfer of data from one location to another, for example, using a hard drive, thumb drive, or other data storage mechanism. System 600 also includes program product 608 (e.g., related to implementing a method of determining a cognitive load of a sensorized device user and/or adjusting an interface between a user and a sensorized device as described herein) stored on a computer or machine readable medium, such as, for example, one or more of various types of memory, such as memory 606 of server 602, that is readable by the server 602, to facilitate, for example, a guided search application or other executable by one or more other communication devices, such as 614 (schematically shown as a desktop or personal computer), IPA device 616, or VR device 620. In some aspects, system 600 optionally also includes at least one database server, such as, for example, server 610 associated with an online website having data stored thereon searchable either directly or through search engine server 602. System 600 optionally also includes one or more other servers positioned remotely from server 602, each of which are optionally associated with one or more database servers 610 located remotely or located local to each of the other servers. The other servers can beneficially provide service to geographically remote users and enhance geographically distributed operations.

As understood by those of ordinary skill in the art, memory 606 of the server 602 optionally includes volatile and/or nonvolatile memory including, for example, RAM, ROM, and magnetic or optical disks, among others. It is also understood by those of ordinary skill in the art that although illustrated as a single server, the illustrated configuration of server 602 is given only by way of example and that other types of servers or computers configured according to various other methodologies or architectures can also be used. Server 602 shown schematically in FIG. 6, represents a server or server cluster or server farm and is not limited to any individual physical server. The server site may be deployed as a server farm or server cluster managed by a server hosting provider. The number of servers and their architecture and configuration may be increased based on usage, demand and capacity requirements for the system 600. As also understood by those of ordinary skill in the art, other user communication devices 614, 616, 620 in these aspects, for example, can be a laptop, desktop, tablet, intelligent personal assistant (IPA) device or personal digital assistant (PDA), a VR device, cell phone, server, or other types of computers. As known and understood by those of ordinary skill in the art, network 612 can include an internet, intranet, a telecommunication network, an extranet, or world wide web of a plurality of computers/servers in communication with one or more other computers through a communication network, and/or portions of a local or other area network.

As further understood by those of ordinary skill in the art, exemplary program product or machine readable medium 608 is optionally in the form of microcode, programs, cloud computing format, routines, and/or symbolic languages that provide one or more sets of ordered operations that control the functioning of the hardware and direct its operation. Program product 608, according to an exemplary aspect, also need not reside in its entirety in volatile memory, but can be selectively loaded, as necessary, according to various methodologies as known and understood by those of ordinary skill in the art.

As further understood by those of ordinary skill in the art, the term "computer-readable medium" or "machine-readable medium" refers to any medium that participates in providing instructions to a processor for execution. To illustrate, the term "computer-readable medium" or "machine-readable medium" encompasses distribution media, cloud computing formats, intermediate storage media, execution memory of a computer, and any other medium or device capable of storing program product 608 implementing the functionality or processes of various aspects of the present disclosure, for example, for reading by a computer. A "computer-readable medium" or "machine-readable medium" may take many forms, including but not limited to, non-volatile media, volatile media, and transmission media. Non-volatile media includes, for example, optical or magnetic disks. Volatile media includes dynamic memory, such as the main memory of a given system. Transmission media includes coaxial cables, copper wire and fiber optics, including the wires that comprise a bus. Transmission media can also take the form of acoustic or light waves, such as those generated during radio wave and infrared data communications, among others. Exemplary forms of computer-readable media include a floppy disk, a flexible disk, hard disk, magnetic tape, a flash drive, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave, or any other medium from which a computer can read.

Program product 608 is optionally copied from the computer-readable medium to a hard disk or a similar intermediate storage medium. When program product 608, or portions thereof, are to be run, it is optionally loaded from their distribution medium, their intermediate storage medium, or the like into the execution memory of one or more computers, configuring the computer(s) to act in accordance with the functionality or method of various aspects. All such operations are well known to those of ordinary skill in the art of, for example, computer systems.

To further illustrate, in certain aspects, this application provides systems that include one or more processors, and one or more memory components in communication with the processor. The memory component typically includes one or more instructions that, when executed, cause the processor to provide information that causes images, auditory information, related data, and/or the like to be displayed or played (e.g., via communication devices 614, 616 or the like) and/or receive information from other system components and/or from a system user (e.g., via communication devices 614, 616, or the like).

In some aspects, program product 608 includes non-transitory computer-executable instructions which, when executed by electronic processor 604 perform at least: receiving at least a first substantially real-time pupillometric data value from a user (e.g., via wearable detection device 618) of an intelligent personal assistant (IPA) device (e.g., IPA device 616) or via VR headset 620 from at least a first time point; receiving at least a first substantially real-time unconstrained environmental data value (e.g., via wearable detection device 618 or via VR headset 620) from at least one location proximal to the user from the first time point, and isolating one or more cognitive load factors from one or more non-cognitive load factors influencing the user at the first time point based at least upon the first substantially real-time pupillometric data value and the first substantially real-time unconstrained environmental data value. In certain aspects, program product 608 includes non-transitory computer-executable instructions which, when executed by electronic processor 604 perform at least: receiving at least a first substantially real-time pupillometric data value (e.g., via wearable detection device 618 or via VR headset 620) from a user of a sensorized device (e.g., IPA device 616 or VR headset 620) from at least a first time point and at least a first substantially real-time unconstrained environmental data value (e.g., via wearable detection device 618 or via VR headset 620) from at least one location proximal to the user from the first time point, and at least a second substantially real-time pupillometric data value (e.g., via wearable detection device 618 or via VR headset 620) from the user from at least a second time point and at least a second substantially real-time unconstrained environmental data value (e.g., via wearable detection device 618 or via VR headset 620) from at least one location proximal to the user from the second time point, when the user is using the sensorized device at least proximal to the first time point and/or the second time point; isolating one or more cognitive load factors from one or more non-cognitive load factors influencing the user at the first and second time points based at least upon the first substantially real-time pupillometric data value, the first substantially real-time unconstrained environmental data value, the second substantially real-time pupillometric data value, and/or the second substantially real-time unconstrained environmental data value to determine a cognitive load change in the user between the first and second time points to produce a determined cognitive load change; and adjusting at least one function of the sensorized device (e.g., IPA device 616 or VR headset 620) at least proximal to the first time point and/or the second time point based at least in part on the determined cognitive load change in the user. Other exemplary executable instructions that are optionally performed are described further herein.

Additional details relating to computer systems and networks, databases, and computer program products are also provided in, for example, Peterson, *Computer Networks: A Systems Approach*, Morgan Kaufmann, 5th Ed. (2011), Kurose, *Computer Networking: A Top-Down Approach*, Pearson, 7th Ed. (2016), Elmasri, *Fundamentals of Database Systems*, Addison Wesley, 6th Ed. (2010), Coronel, *Database Systems: Design, Implementation, & Management*, Cengage Learning, 11th Ed. (2014), Tucker, *Programming Languages, McGraw-Hill Science/Engineering/Math,* 2nd Ed. (2006), and Rhoton, *Cloud Computing Architected: Solution Design Handbook*, Recursive Press (2011), which are each incorporated by reference in their entirety.

Example: Cognitive Load Aware User Interfaces for Mixed Reality Environments

1. Introduction

The present disclosure includes the development of artificial intelligence methodology that 1) enables eye tracking-based cognitive load estimation in unconstrained, real life-like environments ("in the wild") to 2) improve IPAs through more natural interaction mechanisms. Cognitive load estimation 1) is possible in unconstrained environments based on head-worn human- and world-facing sensors, and 2) enables more natural interaction paradigms between humans and IPAs in mixed reality environments.

The present disclosure includes the development of a machine learning-based, algorithmic solution to estimate cognitive load changes in the wild based on a head-worn spectacle frame with integrated optical cameras that supply eye and world (human and world-facing, respectively) video feeds in real time. The algorithm is based on a causal model of pupil dilation (see, FIG. 4) to estimate the inverse probability of cognitive load change given observed pupillometry and environmental conditions. The data used to develop this method is available through a controlled user study that allows for precise calibration of camera parameters as well as cognitive load. This development results in a methodology for eye tracking-based cognitive load estimation in unconstrained, real world-like environments.

The present disclosure also involves using a human-centered design process that shows how ubiquitous cognitive load awareness can avoid user frustration in auditory, verbal, and visual interactions with IPAs in mixed reality environments. The development includes integrating the algorithmic solutions described herein in a mixed reality environment to evaluate their performance across diverse tasks under real world conditions. User's satisfaction to the system with and without cognitive load detection is compared after interaction with IPAs involving tasks with different levels of cognitive load. This development task establishes cognitive load awareness as an enabling component for more natural IPA interactions.

The role of pupillary response as an indicator for cognitive load has been well studied. A number of metrics have been developed to define the relationship between pupil size and cognitive load. Some have developed a task-evoked pupillary response metric (TEPR), relating pupil diameter changes following task onset to cognitive load levels. However, as TEPR is not able to disentangle the light reflex from cognitive load reflex. Others have developed an Index of Pupillary Activity, inspired by the closed source Index of Cognitive Activity, which enables classification of cognitive load level by transforming the pupil diameter signal to the frequency domain and detecting rapid oscillations in pupil diameter, enabling "moment-to-moment" pupil size analysis independent of baseline. These latter techniques aim to disentangle the light reflex from cognitive load reflex. However, experiments have been done in the absence of natural light, that is with a fixed range of luminescence.

Others have attempted to achieve cognitive load estimation in-the-wild by developing a classification framework for task evoked pupillary response using user input to indicate task onset, limiting detection of cognitive load to known regions preceding and following task onset. Some have established a simple model estimating cognitive load under varying light conditions by first measuring average pupil diameter under a set of fixed lighting conditions followed by measuring task evoked pupillary response under each same lighting condition. While this experimental setup does not replicate true environmental conditions, the results established a proof-of-concept that a disentanglement or isolation of pupillary response to lighting condition and cognitive state changes is possible.

Some embodiments of the approaches disclosed herein build off of recent advancements in computer vision and eye-tracking technology. Using these advancements, an approach is developed that estimates environmental and focal object luminescence observed by the user using RGB video feed, as well as models the impact of eye movements such as blinks and vergence on pupil diameter, enabling cognitive load estimation in the wild using a wearable eye-tracker.

Some experiments leading to the developments disclosed herein were able to demonstrate that environmental factors impacting pupil diameter can be estimated from RGB video feed. Initial work focuses on developing a robust method for estimating the ambient light experienced by the user. In contrast to existing approaches, rather than approximating absolute pupil diameter correlations to brightness levels, temporal environmental brightness information is leveraged to develop a likelihood of pupil diameter change in response to the brightness change across the time period. As part of this analysis, a leading phenomenon is observed between pupil response and luminescence measurement. As luminescence measurement is based on a high-speed camera with a 100° field-of-view (FOV) in this aspect, eye motion leads head motion. Thus, the pupil can be responding to a shift in ambient light in a region of the environment on the edges of the FOV of the camera. To address this observation, focal object brightness is incorporated into the causal model to capture the brightness levels at the region of the user's gaze.

2. Methods

Estimating Cognitive Load Based on Eye Tracking "in the Wild"

An objective is to develop an algorithmic solution to estimate cognitive load changes in unconstrained environments and in real time based on a head-worn mixed reality device with integrated human and world-facing optical cameras.

The primary barrier to estimating cognitive load from eye tracking in the wild is the list of confounding factors that cause pupil dilation and constriction. To overcome this challenge, a causal model of pupil dilation (FIG. 4) is built through which the inverse probability is obtained, i.e., the presence of a cause given the effect—in the present case, the presence of cognitive load change given pupil diameter change and other conditions: P(Cognitive State Change|Pupil Diameter Change=ΔPD, Focal Brightness Change=ΔFB, Ambient Light Change=ΔAL). Estimating the probabilities used for this analysis becomes possible through careful combination of computer vision algorithms, which automatically estimate critical quantities from eye- and world-facing video, and precisely controlled user studies to evoke cognitive load changes.

Hardware: To collect eye- and world-facing data, the commercially available research grade Pupil Core system is used due to the open source nature of its software and availability of inserts for common mixed reality headsets. The Pupil Core eye tracker consists of two human-facing eye cameras and one wide-angle world-facing camera. The eye- and world-facing cameras are co-calibrated such that the gaze position in the world camera feed is known. The acquisition parameters of the world-facing camera (including integration time, aperture, ISO, and white balance) can be accessed and controlled for to obtain unbiased estimates of scene brightness.

Pupil Diameter Change: Pupil diameter changes are detected from the commercially available, open source Pupil Labs software and Pupil Core API. This approach is able to achieve a gaze accuracy of 0.60°.

Figure 7:
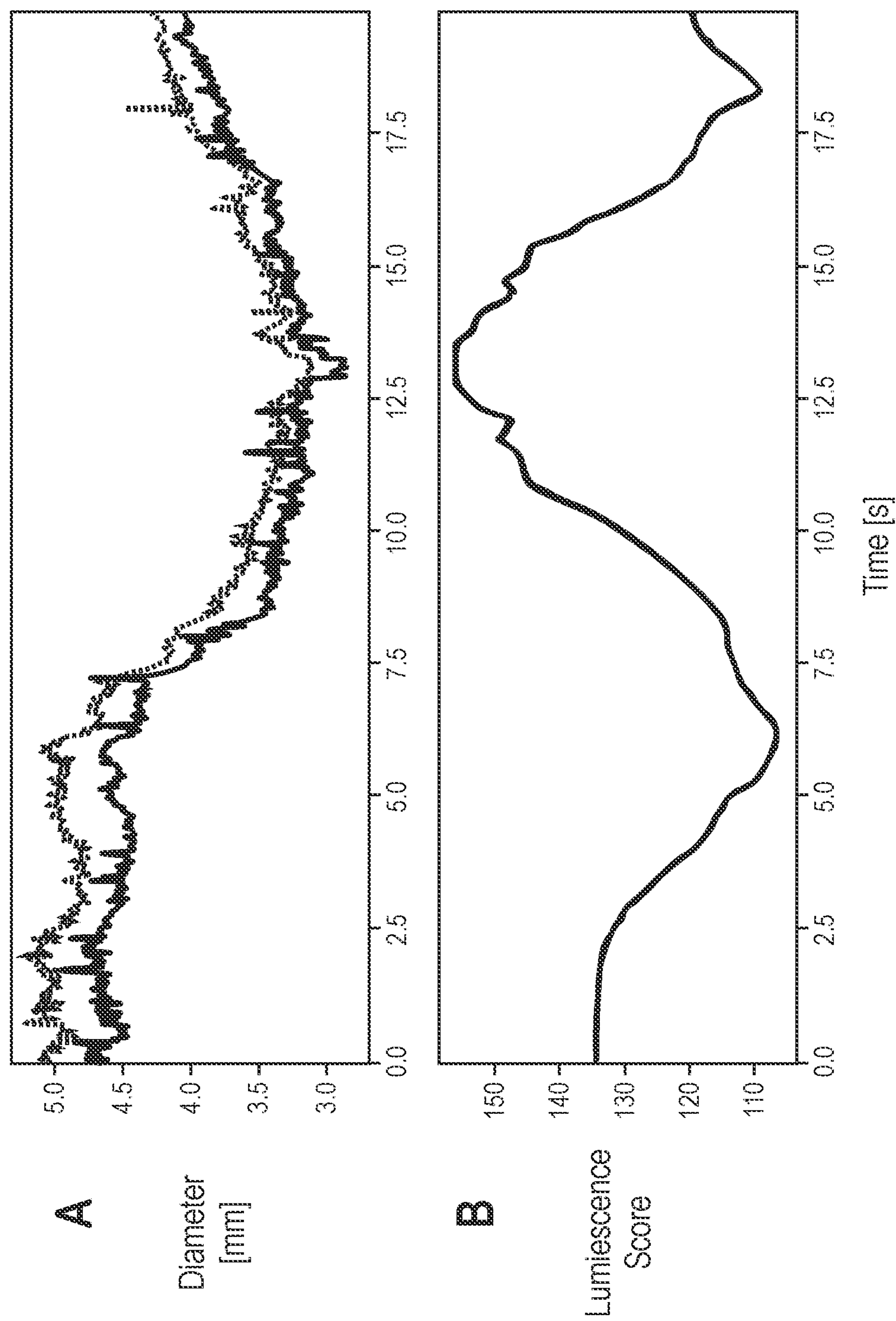
FIG. 7 (Panels A and B) are plots that show results from an ambient light measurement pipeline in which Panel A shows pupil diameter in millimeters (Y-axis) versus time in seconds (X-axis) and Panel B shows the luminescence score (Y-axis) versus time in seconds (X-axis).

Ambient Light Measurement: Ambient light changes have been found to be a major barrier to accurate cognitive load estimation in the wild. As a result, much prior work has controlled for lighting condition changes. However, such controls do not exist in real-world applications. While standard computer imaging techniques enable one to measure overall brightness of an image, commercially available cameras (including the high-speed world-facing camera used in the Pupil Core) have automatic adjustments to changing lighting conditions which, if not accounted for, prevent quantitative ambient brightness characterization from world-facing video. Therefore, in order to measure the brightness of the environment perceived by the user, the world-facing camera's integration time, aperture setting, ISO value, and white balance to convert pixel intensities to a reference camera speed are taken into account. This allows for quantitative monitoring of temporal change of luminescence in the world-facing camera video feed which serves as a valid indicator of changes of the ambient light brightness in the environment. Using the pixel intensities converted to the reference speed and represented in CIE Lab color space, an ambient luminescence score is developed by averaging the luminescence over every frame. An analysis of pupil diameter changes in relation to this score is provided in FIG. 7.

Focal Object Brightness: To obtain a measure for the focal object brightness, the method follows the image processing pipeline established above for ambient light measurement. Following conversion of the world-facing video feed from RGB to reference speed and CIE Lab color space, the focal object or region is isolated using gaze tracking data available through the Pupil Core API of the eye tracker. A focal region-of-interest (ROI) is isolated and a focal object brightness score is calculated via weighted averaging of the luminescence within the ROI.

Isolating Cognitive Load: Given the above methods, we are able to measure both, ambient light and focal brightness changes, as well as pupil diameter changes in real time with >30 Hz. With estimations of the conditional probabilities in the causal model of pupil dilation shown in FIG. 4, the inverse probability of cognitive load change given the evidence can be estimated, that in this case are measured using human- and front-facing cameras. Estimating the conditional probabilities typically uses a controlled experimental setup that is implemented through a user study, as described below.

User Study: Volunteer participants can be recruited, who are asked to complete well defined and validated visual, auditory, and dictation experiments that are used in the context of cognitive effort. While these experiments are conducted in controlled settings, varying environmental conditions are introduced, including ambient light and focal brightness changes and participants are asked to both, hold still and navigate freely in the environment throughout the study. All eye- and world-facing camera video feeds are recorded to create an eye tracking dataset captured under indoor, close to real world conditions. Each user study provides 45 minutes of video including 20 cognitive load changes.

Algorithm Development and Validation: Based on the dataset collected in the user study, the machine learning algorithm for cognitive load estimation in the wild is developed and validated using a leave-one-subject-out cross validation. The method is classified to be successful if the algorithm identifies>80% of the cognitive load changes irrespective of other environmental conditions.

While light changes are the most significant confounding factor when trying to estimate cognitive state change under normal environmental conditions via eye tracking, other factors can also be incorporated in the model, such as those derived from eye tracking, including blinks and saccades. Some embodiments use alternative approach that directly predicts the likelihood of cognitive load change based on the observed quantities using, for example, random forests or deep neural networks.

Understanding the Benefit of Cognitive Load Aware Interaction

Another goal is to study how ubiquitous cognitive load awareness benefits user interaction and eliminates frustration during interactions with IPAs in mixed reality environments.

Human-centered Design Process: Visual, auditory, and dictation tasks are designed to be achieved through interactions with an IPA. The human-centered design process is adopted to identify primary causes of user frustration as the cognitive effort of prompted tasks increases to iteratively develop a cognitive load aware interaction that increases user satisfaction and perceived cognitive load.

User Study: Based on the findings in the human-centered design phase, a prototypical IPA interaction on a mixed reality device is implemented. The cognitive load estimation algorithm developed above is integrated into the prototype to adapt its interaction strategy whenever increased cognitive effort is detected. Volunteer participants are asked to complete visual, auditory, and dictation tasks intended to stimulate drastic changes in cognitive effort over time. A within-subject user study is conducted where, in a randomized order, these experiments are delivered under two conditions: 1) with a cognitive load aware interaction, and 2) without cognitive load aware interaction. User's subjective task load are evaluated using the NASA TLX survey complemented with a survey on usability and user experience.

In some embodiments, rather than adapting the interactions based on live cognitive load estimates, the interactions are guided by the expected cognitive effort of any given task based on the literature. In addition, eye tracking data for post hoc analysis of cognitive effort is optionally acquired to correctly interpret the user surveys.

While the foregoing disclosure has been described in some detail by way of illustration and example for purposes of clarity and understanding, it will be clear to one of ordinary skill in the art from a reading of this disclosure that various changes in form and detail can be made without departing from the true scope of the disclosure and may be practiced within the scope of the appended claims. For example, all the methods, devices, systems, computer readable media, and/or component parts or other aspects thereof can be used in various combinations. All patents, patent applications, websites, other publications or documents, and the like cited herein are incorporated by reference in their entirety for all purposes to the same extent as if each individual item were specifically and individually indicated to be so incorporated by reference.

What is claimed is:

1. A method of adjusting an interface between a user and a sensorized device, the method comprising:

receiving at least a first substantially real-time pupillometric data value from the user from at least a first time point and at least a first substantially real-time unconstrained environmental data value from at least one location proximal to the user from the first time point;

receiving at least a second substantially real-time pupillometric data value from the user from at least a second time point and at least a second substantially real-time unconstrained environmental data value from at least one location proximal to the user from the second time point, wherein the user is using the sensorized device at least proximal to the first time point and/or the second time point;

isolating one or more cognitive load factors from one or more non-cognitive load factors influencing the user at the first and second time points based at least upon the first substantially real-time pupillometric data value, the first substantially real-time unconstrained environmental data value, the second substantially real-time pupillometric data value, and/or the second substantially real-time unconstrained environmental data value to determine a cognitive load change in the user between the first and second time points to produce a determined cognitive load change, wherein determining the cognitive load change in the user between the first and second time points comprises determining an inverse probability of the cognitive load change given the first substantially real-time pupillometric data value, the first substantially real-time unconstrained environmental data value, the second substantially real-time pupillometric data value, and/or the second substantially real-time unconstrained environmental data value; and, adjusting at least one function of the sensorized device at least proximal to the first time point and/or the second time point based at least in part on the determined cognitive load change in the user, thereby adjusting the interface between the user and the sensorized device.

2. The method of claim 1, wherein the user is using at least one sensorized device at least proximal to the first time point and wherein the method further comprises adjusting at least one function of the sensorized device at least proximal to the first time point based at least in part on the determined cognitive load of the user.

3. The method of claim 1, wherein the sensorized device comprises a computer.

4. The method of claim 1, wherein the sensorized device and a computer are operably connected to one another.

5. The method of claim 1, wherein the first and/or second substantially real-time pupillometric data value comprises a pupil diameter, a pupil radius, a pupil size, a blink rate, a saccade rate, or other measure of at least one eye of the user.

6. The method of claim 1, wherein the first and/or second substantially real-time unconstrained environmental data value comprises a measure of at least one visual property.

7. The method of claim 6, wherein the visual property comprises an ambient light measure and/or a focal brightness measure.

8. The method of claim 1, wherein the first and/or second substantially real-time unconstrained environmental data value comprises a measure of at least one visual property, at least one auditory property, at least one dictation property, at least one physiological property or state of the user, and/or at least one physical property of an environment external to the user.

9. The method of claim 1, comprising receiving the first and/or second substantially real-time pupillometric data value and/or the first and/or second substantially real-time unconstrained environmental data value from at least one detection device.

10. The method of claim 9, wherein the detection device comprises at least one video camera.

11. The method of claim 9, wherein a wearable device comprises the detection device, which wearable device is worn by the user.

12. The method of claim 11, wherein the wearable device comprises a head-mounted display, a headphone, a spectacle frame, and/or an article of clothing.

13. The method of claim 1, wherein the sensorized device comprises an intelligent personal assistant (IPA) device.

14. The method of claim 1, wherein the sensorized device comprises a virtual reality (VR) device.

15. A system, comprising at least one controller that comprises, or is capable of accessing, computer readable media comprising non-transitory computer executable instructions which, when executed by at least one electronic processor, perform at least:

receiving at least a first substantially real-time pupillometric data value from a user of a sensorized device from at least a first time point and at least a first substantially real-time unconstrained environmental data value from at least one location proximal to the user from the first time point, and at least a second substantially real-time pupillometric data value from the user from at least a second time point and at least a second substantially real-time unconstrained environmental data value from at least one location proximal to the user from the second time point, when the user is using the sensorized device at least proximal to the first time point and/or the second time point;

isolating one or more cognitive load factors from one or more non-cognitive load factors influencing the user at the first and second time points based at least upon the first substantially real-time pupillometric data value, the first substantially real-time unconstrained environmental data value, the second substantially real-time pupillometric data value, and/or the second substantially real-time unconstrained environmental data value to determine a cognitive load change in the user between the first and second time points to produce a determined cognitive load change, wherein determining the cognitive load change in the user between the first and second time points comprises determining an inverse probability of the cognitive load change given the first substantially real-time pupillometric data value, the first substantially real-time unconstrained environmental data value, the second substantially real-time pupillometric data value, and/or the second substantially real-time unconstrained environmental data value; and, adjusting at least one function of the sensorized device at least proximal to the first time point and/or the second time point based at least in part on the determined cognitive load change in the user.

16. A non-transitory computer readable medium comprising computer executable instructions which, when executed by at least one electronic processor, perform at least:

receiving at least a first substantially real-time pupillometric data value from a user of a sensorized device from at least a first time point and at least a first substantially real-time unconstrained environmental data value from at least one location proximal to the user from the first time point, and at least a second substantially real-time pupillometric data value from the user from at least a second time point and at least a second substantially real-time unconstrained environmental data value from at least one location proximal to the user from the second time point, when the user is using the sensorized device at least proximal to the first time point and/or the second time point;

isolating one or more cognitive load factors from one or more non-cognitive load factors influencing the user at the first and second time points based at least upon the first substantially real-time pupillometric data value, the first substantially real-time unconstrained environmental data value, the second substantially real-time pupillometric data value, and/or the second substantially real-time unconstrained environmental data value to determine a cognitive load change in the user between the first and second time points to produce a determined cognitive load change, wherein determining the cognitive load change in the user between the first and second time points comprises determining an inverse probability of the cognitive load change given the first substantially real-time pupillometric data value, the first substantially real-time unconstrained environmental data value, the second substantially real-time pupillometric data value, and/or the second substantially real-time unconstrained environmental data value; and, adjusting at least one function of the sensorized device at least proximal to the first time point and/or the second time point based at least in part on the determined cognitive load change in the user.

* * * * *